United States Patent [19]

Kurano et al.

[11] Patent Number: 5,113,018
[45] Date of Patent: May 12, 1992

[54] METHOD OF PRODUCING N-ALKYLAMINOPHENOLS

[75] Inventors: Yoshito Kurano, Yamaguchi; Masato Kawamura, Osaka; Masahiro Kondo, Yamaguchi; Michio Tanaka, Yamaguchi; Sanehiro Yamamoto, Yamaguchi, all of Japan

[73] Assignee: Mitsui Petrochemical Industries, Ltd., Tokyo, Japan

[21] Appl. No.: 538,719

[22] Filed: Jun. 15, 1990

[30] Foreign Application Priority Data

Jun. 16, 1989 [JP] Japan ................................. 1-153899
Jun. 16, 1989 [JP] Japan ................................ 10-153900

[51] Int. Cl.$^5$ .......................................... C07C 209/18
[52] U.S. Cl. .................................... 564/403; 564/402
[58] Field of Search ............................... 564/402, 403

[56] References Cited

U.S. PATENT DOCUMENTS 3,102,913 12/1963 Werner et al. ...................... 564/403

FOREIGN PATENT DOCUMENTS 473490   5/1951  Canada ............................. 564/402
0197633 10/1986 European Pat. Off. ............ 564/403
8156    of 1890 United Kingdom ................ 564/403
415945   9/1934 United Kingdom ................ 564/403

Primary Examiner—Glennon H. Hollrah
Assistant Examiner—Shailendra Kumar
Attorney, Agent, or Firm—Sherman & Shalloway

[57] ABSTRACT

N-alkyl amino phenols, such as N-ethyl-m-amino phenol are produced in high yield and with high purity by reacting a divalent phenol, such as resorcinol, with an alkylamine, such as ethylamine, in the absence of catalyst and solvent, at a temperature of 120°–210° C. under elevated pressure in an inert gas atmosphere. In a first embodiment, the resulting reaction mixture is acidified to convert the N-alkylaminophenol to its water soluble salt and the resulting aqueous layer is separated from the oily layer. The aqueous layer is rendered alkaline to liberate N-alkylaminophenol as an oily layer. The N-alkyl-aminophenol oily layer is then separated from the aqueous layer and distilled. In an alternative embodiment, the reaction mixture resulting from the reaction between the divalent phenol and alkylamine is combined with an aqueous solution of an alkali to convert unreacted phenol to its water soluble salt while the product N-alkylaminophenol remains in an oily phase which is separated from the aqueous phase. An organic solvent is used as an extractant. The recovered N-alkylaminophenol organic solution is then distilled to recover N-alkylaminophenol. Purities of the recovered N-alkylaminophenol in excess of 95% can be achieved.

14 Claims, No Drawings

METHOD OF PRODUCING N-ALKYLAMINOPHENOLS

This invention relates to a method of producing N-alkylaminophenols which are suitably used as intermediates for the production of heat or pressure sensitive dyes, xanthene dyes or fluorescent dyes.

It is already known that the reaction of a divalent phenol and an organic amine compound in the absence of a catalyst provides an N-alkylaminophenol, as described in Japanese Patent Application Laid-open No. 48-28429. The use of a catalyst such as a metal compound in the reaction is also known, as described in Japanese Patent Application Laid-open No. 55-105648. In these prior methods, the resultant N-alkylaminophenols are purified by such a method as distillation, recrystallization or extraction with an organic solvent, but these purification methods are in short of efficiency. Further, the prior production methods have a low conversion of divalent phenols, but also produce a significant amount of undesirable by-products such as phenylenediamines so that the reaction efficiency is low.

It is, therefore, an object of the invention to provide a method of producing N-alkylaminophenols which enables simple and efficient purification of the reaction products.

It is a further object of the invention to provide a method of producing N-alkylaminophenols in a high conversion rate of divalent phenols and a reduced production of undesirable by-products to ensure a high yield production of the N-alkylaminophenols.

In accordance with the invention, there is provided an improvement in the production of an N-alkylaminophenol which comprises the reaction of a divalent phenol with an alkylamine to provide a reaction mixture and recovering the N-alkylaminophenol from the reaction mixture, the improvement comprising:

(a) adding an aqueous solution of an acid to the reaction mixture to provide a two-phase mixture composed of an aqueous phase which contains a water soluble acid salt of the resultant N-alkylaminophenol and an organic phase which contains an unreacted divalent phenol;

(b) separating the unreacted divalent phenol as an organic solution by extraction of the two-phase mixture with an organic solvent, to leave an aqueous solution;

(c) neutralizing the water soluble acid salt of N-alkylaminophenol in the aqueous solution with an aqueous solution of an alkali to provide an oily phase of N-alkylaminophenol; and (d) separating the oily phase and distilling it to recover the N-alkylaminophenol.

The divalent phenol used in the invention is preferably represented by the general formula (I):

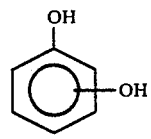

and it may be exemplified by, for example, resorcinol or hydroquinone.

In turn, the alkylamine used in the invention is preferably represented by the general formula (II):

wherein $R^1$ and $R^2$ represent independently a hydrogen or an alkyl of 1-6 carbons with both $R^1$ and $R^2$ being not hydrogens. The alkylamine thus includes a primary amine and a secondary amine. The primary amine may be exemplified by, for example, methylamine, ethylamine, n-propylamine, isopropylamine, n-butylamine, isobutylamine, n-amylamine, isoamylamine or cyclohexylamine, while the secondary amine may be exemplified by, for example, dimethylamine, diethylamine, di-n-propylamine, diisopropylamine, di-n-butylamine, diisobutylamine, di-n-amylamine, diisoamylamine or dicyclohexylamine.

The amination reaction of the divalent phenol with the alkylamine provides an N-alkyl- or N,N-dialkylaminophenol as represented by the general formula (III) as shown below:

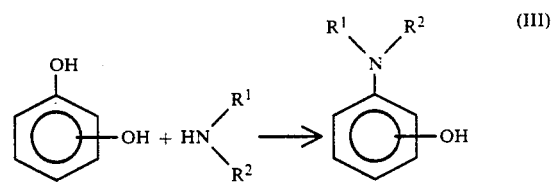

wherein $R^1$ and $R^2$ are the same as before. As seen above, the use of a primary amine provides N-alkylaminophenol as a main product whereas the use of a secondary amine provides N,N-dialkylaminophenol as a main product. Herein the specification, the term, "N-alkylaminophenol" includes N,N-dialkylaminophenol.

In the amination reaction, the alkylamine is used in a molar ratio of the alkylamine to the divalent phenol of 0.4-1.2, preferably in a molar ratio of 0.5-1.0, not only to increase the conversion rate of the divalent phenol but also to suppress the production of by-products such as phenylenediamines and to improve the selectivity of the reaction to the N-alkylaminophenol.

The reaction is carried out at a temperature preferably of 120°-210° C., more preferably of a temperature of 130°-200° C., to raise the reaction efficiency and to suppress the production of by-products such as a tar material. The above reaction temperature also enables the reaction to proceed under a low pressure. Thus, the reaction may be carried out under a pressure of from normal pressure to 40 Kg/cm$^2$G, preferably of a pressure in the range of 3-20 Kg/cm$^2$G under an inert gas atmosphere such as nitrogen, over a period of 1-5 hours, preferably of 2-4 hours.

It is preferred that the amination reaction is carried out in the absence of a solvent, however, there may be used an organic solvent, if necessary, which is inactive in the reaction such as phenolic solvents.

It is further preferred that the amination reaction is effected in the absence of a catalyst, however, a catalyst may be used, if necessary. The catalyst usable includes, for example, phosphoric acid salts, ammoninum salts or acetic acid salts. When these catalysts are used in the amination reaction, they are separated prior to the procedures for the purification and recovery of the N-alkylaminophenol. The invention is not specifically limited in the method of separating and removing the catalyst from the reaction mixture. Thus the catalyst may be separated by, for instance, filtration, layer separation or extraction, according to the catalyst used.

After the reaction, the catalyst is removed from the reaction mixture when it is used in the reaction, and then, according to the invention, an aqueous solution of an acid is added to the reaction mixture to convert the resultant N-alkylaminophenol to a water soluble acid salt. The acid may be any acid either inorganic or organic provided that it can form a water soluble salt with the N-alkylaminophenol. There may be mentioned as such an acid, for example, an inorganic acid such as hydrochloric acid, sulfuric acid or phosphoric acid, or an organic acid such as p-toluenesulfonic acid or methanesulfonic acid, among which is preferred a mineral acid such as hydrochloric acid or sulfuric acid. The acid is used in a molar ratio of the acid to the N-alkylaminophenol usually of 0.5-2, preferably of 0.7-1.5, as an aqueous solution usually of a concentration of 20-80% by weight, preferably of a concentration of 30-70% by weight.

The addition of the aqueous solution of an acid to the reaction mixture provides a two-phase mixture composed of an aqueous phase which contains a water soluble acid salt of the resultant N-alkylaminopenol and an organic phase which contains an unreacted divalent phenol. The two-phase mixture is then extracted with an organic solvent so that the unreacted divalent phenol and the other materials soluble in the organic solvent are separated into the organic solvent, to leave an aqueous solution which contains the water soluble acid salt of N-alkylaminopenol.

The organic solvent used is such that the divalent phenol used is highly soluble therein, and accordingly the solvent includes, for example, a ketone or an ether. More specifically, there may be mentioned as such a ketone, for example, methyl n-propyl ketone, methyl n-butyl ketone, or methyl isobutyl ketone, and as such an ether, for example, diethyl ether, diisopropyl ether or di-n-butyl ether.

The extraction is carried out in such a manner that an organic solvent is added to the two-phase mixture in a weight ratio of the organic solvent to the unreacted divalent phenol in the mixture of 0.1-2, preferably of 0.5-1.5 per a single extraction operation, at a temperature of from normal temperature to 100° C. This extraction procedure is repeated several times, if necessary, so that substantially all the unreacted divalent phenol and the other materials soluble in the solvent are extracted into the solvent.

An aqueous solution of an alkali is then added to the aqueous solution separated from the organic phase to adjust the solution at a pH of about 5-9, preferably of 6-8, to neutralize the acid salt and to liberate free N-alkylaminopenol as an oily layer. The alkali is preferably sodium hydroxide and is used as an aqueous solution of a concentration of 5-50% by weight, preferably of 10-40% by weight. The liberated free N-alkylaminophenol may be separated by extraction with an organic solvent usually at a temperature from normal temperature to 100° C., preferably of 30°-60° C. The extraction efficiency may be improved by adjusting properly the concentration or amount of the alkali solution used, or by adding a neutral salt to the aqueous solution.

Alternatively, the oily layer is directly separated from an aqueous layer. The separated oily phase is mainly composed of the N-alkylaminophenols, and pure N-alkylaminophenols are recovered by distillation of the oily phase. The distillation is carried out preferably at a bottom temperature of from normal temperature to 180° C. under from normal pressure to a reduced pressure of about 10 mmHg.

The recovered unreacted divalent phenol may be reused as it is for the amination reaction, or may be distilled to remove the solvent therefrom, and further purified for reuse in the amination reaction.

In accordance with the invention, there is provided a further improvement in the production of an N-alkylaminophenol which comprises:

(a) adding an aqueous solution of an alkali to the reaction mixture after the reaction to provide a two-phase mixture composed of an aqueous phase which contains a water soluble alkali salt of the unreacted divalent phenol and an organic phase which contains the resultant N-alkylaminophenol;

(b) separating the N-alkylaminophenol from the two-phase mixture by extraction with an organic solvent as an organic solution; and (c) distilling the organic solution to recover the N-alkylaminophenol.

After the reaction, the catalyst is removed from the reaction mixture when it is used in the reaction, and then, according to the invention, an aqueous solution of an alkali is added to the reaction mixture to provide a two-phase mixture composed of an aqueous phase which contains a water soluble alkali salt of the unreacted divalent phenol and an organic phase which contains the resultant N-alkylaminophenol. The aqueous alkali solution used is preferably a solution of sodium hydroxide of a concentration of 5-50% by weight, preferably of 10-40% by weight. The alkali is used in an amount of 1-3 equivalents, preferably of 1.5-2.5 equivalents per mole of the unreacted divalent phenols.

Then, the two-phase mixture is extracted with an organic solvent to separate the N-alkylaminophenol and the other organic materials soluble in the solvent as an organic solution.

The organic solvent used is such that aminophenols are highly soluble therein, and accordingly the solvent includes, for example, a ketone or an ether. More specifically, there may be mentioned as such a ketone, for example, methyl n-propyl ketone, methyl n-butyl ketone, or methyl isobutyl ketone, and as such an ether, for example, diethyl ether, diisopropyl ether or di-n-butyl ether.

The extraction is carried out in such a manner that an organic solvent is added to the mixture in a weight ratio of the organic solvent to the N-alkylaminophenol in the two-phase mixture of 0.1-2, preferably of 0.5-1.5 per a single extraction operation, at a temperature of from normal temperature to 100° C. This extraction procedure is usually repeated several times, so that substantially all the resultant N-alkylaminophenol and the other materials soluble in the solvent are extracted into the solvent.

The separated organic solution is mainly composed of N-alkylaminophenol, and the distillation of the solution provides pure N-alkylaminophenols. The distillation is carried out preferably at a bottom temprature of from normal temperature to 180° C. under from normal pressure to a reduced pressure of about 10 mmHg.

Meanwhile, the aqueous alkali solution separated from the organic phase is adjusted at a pH of about 5-9, preferably of 6-8 by adding thereto an aqueous solution of an acid, to neutralize the alkali salt of the unreacted divalent phenol, to liberate a free divalent phenol as an oily layer. The aqueous acid solution is preferably a solution of sulfuric acid or hydrochloric acid of a concentration of 30-70% by weight.

The liberated free divalent phenol is separated, or extracted and then distilled, for reuse in the amination reaction.

As set forth above, according to the invention, the amination reaction is carried out in a high conversion rate and the production of undesirable by-products is reduced, so that a high reaction efficiency is achieved. Further, since the obtained reaction mixture is efficiently purified according to the invention, a high purity N-alkylaminophenol is readily obtained.

The invention will be more specifically described with reference to examples, however, the invention is not limited thereto.

EXAMPLE SECTION I

A Method Including the Addition of an Acid Solution As the First Step

EXAMPLE 1

Amination Reaction

In a 1.5 liter capacity autoclave provided with a feed line and a stirrer was placed an amount of 110 g of resorcinol. Then the autoclave was purged with nitrogen and closed. After cooling the autoclave in an ice water, the autoclave was evacuated to a pressure of 2-4 mmHg and closed. The feed line was connected to a bomb containing ethylamine and 27.1 g of liquid ethylamine was fed into the autoclave.

After the feed of ethylamine, the autoclave was pressurized to 10 Kg/cm$^2$G. Then the autoclave was heated to 170° C. and the reaction was carried out under stirring at 170° C. over three hours.

After the completion of the reaction, the autoclave was cooled. The reaction product was a viscous liquid which was found to contain 38.9% by weight of resorcinol, 56.5% by weight of N-ethyl-m-aminophenol and 1.4% by weight of N,N'-diethyl-m-phenylenediamine. The conversion rate of resorcinol was 54.9 mol %, the selectivity of N-ethyl-m-aminophenol was 95.7 mol %, and the selectivity of N,N'-diethyl-m-phenylenediamine was 2.0 mol %.

Formation of Sulfuric Acid Salt of Amines

An amount of 54.4 g of a 98% aqueous sulfuric acid solution was added gradually to the reaction mixture, and then 52.2 g of water, followed by stirring the resultant mixture over 30 minutes. Then, an amount of 69 g of methyl isobutyl ketone was added to the mixture to effect oil-water separation. This separation procedure was repeated five times. The obtained aqueous solution was found to contain no resorcinol.

Neutralization of Aqueous Solution

An amount of 174.4 g of a 25% aqueous solution of sodium hydroxide was added gradually to the aqueous solution to neutralize the sulfuric acid salt of the amines. After the neutralization, an amount of 25.4 g of sodium sulfate was added and stirred at 45° C. over 20 minutes. An amount of 84 g of an oily phase was separated from the mixture. The oily phase was found to contain 79.2% by weight of N-ethyl-m-aminophenol and 1.7% by weight of N,N'-diethyl-m-phenylenediamine.

Distillation of Oily Solution

The oily phase was distilled on an oil bath at a temperature of 160°-170° C. under a reduced pressure of 4-14 mmHg, to provide 55.7 g of N-ethyl-m-aminophenol having a purity of 96.6%.

COMPARATIVE EXAMPLE 1

The amination reaction was carried out to a conversion rate of resorcinol of 62 mol % in the same manner as in the Example 1. The selectivity of N-ethyl-m-aminophenol was found 86 mol %.

EXAMPLE 2

Amination Reaction

The amination reaction was carried out at 160° C. and otherwise in the same manner as in the example 1. The reaction product was a viscous liquid which was found to contain 43.5% by weight of resorcinol, 53.2% by weight of N-ethyl-m-aminophenol and 1.1% by weight of N,N'-diethyl-m-phenylenediamine. The conversion rate of resorcinol was 50.4 mol %, the selectivity of N-ethyl-m-aminophenol was 96.6 mol %, and the selectivity of N,N'-diethyl-m-phenylenediamine was 1.7 mol %.

Formation of Sulfuric Acid Salt of Amines

An amount of 107 g of a 50% aqueous sulfuric acid solution was added to the reaction mixture, but no water, and the otherwise in the same manner as in the Example 1, the resultant N-ethyl-m-aminophenol and the other amines were converted to sulfuric acid salts. The unreacted resorcinol in the mixture was extracted into methyl isobutyl ketone.

Neutralization of Aqueous Solution

An amount of 109 g of a 40% aqueous solution of sodium hydroxide was used and no sodium sulfate was added to the mixture, and otherwise in the same manner as in the Example 1, the neutralization and water-oil separation were carried out. The obtained oily phase was found to contain 80.2% by weight of N-ethyl-m-aminophenol and 1.4% by weight of N,N'-diethyl-m-phenylenediamine.

Distillation of Oily Solution

The oily phase was distilled in the same manner as in the Example 1, to provide 51.1 g of N-ethyl-m-aminophenol having a purity of 97.5%.

EXAMPLE 3

Amination Reaction

In a 200 ml capacity autoclave were placed an amount of 40.0 g of resorcinol and 6.09 g of methylamine. Then the autoclave was pressurized to 10 Kg/cm$^2$G, and the reaction was carried out under stirring at 160° C. over two hours.

After the completion of the reaction, the autoclave was cooled. The reaction product was a viscous liquid which was found to contain 46.5% by weight of resorcinol, 46.4% by weight of N-methyl-m-aminophenol and 1.2% by weight of N,N'-dimethyl-m-phenylenediamine. The conversion rate of resorcinol was 49.2 mol %, the selectivity of N-methyl-m-aminophenol was 92.9 mol %, and the selectivity of N,N'-dimethyl-m-phenylenediamine was 2.2 mol %.

Formation and Neutralization of Sulfuric Acid Salt

An amount of 7.3 g of a 50% aqueous sulfuric acid solution was added to the reaction mixture. Then, 10 g of methyl isobutyl ketone was added, and the mixture was extracted at 50° C. The extraction was effected three times. The extraction rate of resorcinol into the ketone was found 93.8%.

The aqueous solution separated from the oily phase was neutralized with a 50% aqueous solution of sodium hydroxide and was then extracted with 10 g of methyl isobutyl ketone. The recovery rate of N-methyl-m-aminophenol into the ketone was 94.5%. The distillation of the methyl isobutyl ketone extract provided N-methyl-m-aminophenol having a purity of 92.5%.

Distillation of Oily Solution

The distillation of the obtained N-methyl-m-aminophenol provided N-methyl-m-aminophenol having a purity of 94.5%.

EXAMPLE 4

Amination Reaction

In a 100 ml capacity autoclave provied with a gas inlet and a stirrer were placed an amount of 20.0 g of resorcinol and 30.0 g of methylamine. Then the reaction was carried out at 160° C. over one hour.

The reaction product was a viscous liquid which was found to contain 54.3% by weight of resorcinol, 42.8% by weight of N-methyl-m-aminophenol and 1.2% by weight of N,N'-dimethyl-m-phenylenediamine. The conversion rate of resorcinol was 42.4 mol %, the selectivity of N-methyl-m-aminophenol was 95.8 mol %, and the selectivity of N,N'-dimethyl-m-phenylenediamine was 2.4 mol %.

Formation and Neutralization of Sulfuric Acid Salt

An amount of 7.3 g of a 50% aqueous sulfuric acid solution was added to 10 g of the reaction mixture. Then, 5 g of methyl isobutyl ketone was added, and the mixture was extracted at 50° C. The extraction was effected four times. The extraction rate of resorcinol into the extract was found 99.9%.

The aqueous solution separated from the ketone extract was neutralized with a 50% aqueous solution of sodium hydroxide and was then extracted with 10 g of methyl isobutyl ketone. The distillation of the methyl isobutyl ketone extract provided N-methyl-m-aminophenol having a purity of 98%.

Distillation of Oily Solution

The distillation of the obtained N-methyl-m-aminophenol provided N-methyl-m-aminophenol having a purity of 98.5%.

COMPARATIVE EXAMPLE 2

Amination Reaction

In a 200 ml capacity autoclave were placed an amount of 40.0 g of resorcinol and 6.09 g of methylamine. Then the reaction was carried out at 160° C. over two hours.

After the completion of the reaction, the autoclave was cooled. The reaction product was a viscous liquid which was found to contain 45.3% by weight of resorcinol, 40.6% by weight of N-methyl-m-aminophenol and 0.8% by weight of N,N'-dimethyl-m-phenylenediamine. The conversion rate of resorcinol was 48.5 mol %, the selectivity of N-methyl-m-aminophenol was 85.0 mol %, and the selectivity of N,N'-dimethyl-m-phenylenediamine was 1.6 mol %.

Formation and Neutralization of Sulfuric Acid Salt

An amount of 16.7 g of a 20% aqueous sulfuric acid solution was added to 10 g of the reaction mixture. Then, 10 g of isopropyl ether was added and the mixture was extracted at 50° C. The extraction was effected three times. The extraction rate of resorcinol into the ether was found 78%.

The remaining aqueous solution was neutralized with a 50% aqueous solution of sodium hydroxide and was then extracted with 10 g of isopropyl ether three times. The resorcinol, N-methyl-m-aminophenol and N,N'-dimethyl-m-phenylenediamine in the aqueous solution were recovered into the isopropyl ether. The removal of the isopropyl ether from the extract provided N-methyl-m-aminophenol having a purity of 77.6%.

Distillation of Oily Solution

The N-methyl-m-aminophenol thus obtained was distilled, but no improvement in purity of the N-methyl-m-aminophenol was attained.

EXAMPLE SECTION II

A Method Including the Addition of an Alkali Solution As the First Step

EXAMPLE 1

Amination Reaction

In a 1.5 liter capacity autoclave provided with a feed line and a stirrer was placed an amount of 110 g of resorcinol. Then the autoclave was purged with nitrogen and closed. After cooling the autoclave in an ice water, the autoclave was evacuated to a pressure of 2-4 mmHg and closed. The feed line was connected to a bomb containing methylamine, and 16.7 g of liquid methylamine was fed into the autoclave.

After the feed of methylamine, the autoclave was pressurized to 10 Kg/cm$^2$G. Then the autoclave was heated to 160° C., and the reaction was carried out under stirring at 160° C. over two hours.

After the completion of the reaction, the autoclave was cooled. The reaction product was a viscous liquid which was found to contain 46.7% by weight of resorcinol, 44.1% by weight of N-methyl-m-aminophenol and 0.9% by weight of N,N'-dimethyl-m-phenylenediamine. The conversion rate of resorcinol was 46.2 mol %, the selectivity of N-methyl-m-aminophenol was 88.3 mol %, and the selectivity of N,N'-dimethyl-m-phenylenediamine was 1.5 mol %.

Purification

An amount of 67.9 g of a 30% aqueous solution of sodium hydroxide was added gradually to 100 g of the reaction mixture, and then the mixture was stirred over 30 minutes. Then, an amount of 50 g of methyl isobutyl ketone was added to the mixture to effect extraction at 35° C. The extraction was repeated four times. The extraction rates of N-methyl-m-aminophenol, resorcinol and N,N'-dimethyl-m-phenylenediamine were 100%, 19.6% and 100%, respectively.

The obtained ketone extract was distilled at a bottom temperature of 160°-170° C. under a reduced pressure of 4-14 mmHg to remove the methyl isobutyl ketone to provide 55.7 g of N-methyl-m-aminophenol having a purity of 81.4%.

Meanwhile, a 50% aqueous solution of sulfuric acid was added to the aqueous solution separated from the ketone layer and then the mixture was extracted twice with methyl isobutyl ketone to recover resorcinol having a purity of 99%.

COMPARATIVE EXAMPLE 1

The amination reaction was carried out to a conversion rate of resorcinol of 62 mol % in the same manner as in the Example 1. The selectivity of N-methyl-m-aminophenol was found 86 mol %.

EXAMPLE 2

The amination reaction was carried out in the same manner as in the Example 1. After the reaction, 113 g of a 30% aqueous solution of sodium hydroxide was added to the reaction mixture, and extraction was effected at 50° C.

The extraction rates of N-methyl-m-aminophenol, resorcinol and N,N'-dimethyl-m-phenylenediamine into methyl isobutyl ketone were 81.3%, 0% and 100%, respectively. The removal of the methyl isobutyl ketone from the extract by distillation provided N-methyl-m-aminophenol having a purity of 97.5%.

EXAMPLE 3

Isopropyl ether was used as an extracting solvent and the extraction was carried out at 50° C., and otherwise in the same manner as in the Example 1, the reaction and consequent purification was carried out. The extraction rates of N-methyl-m-aminophenol, resorcinol and N,N'-dimethyl-m-phenylenediamine into isopropyl ether were 47.6%, 4.5% and 100%, respectively. The removal of the isopropylether from the extract by distillation provided N-methyl-m-aminophenol having a purity of 61.8%.

EXAMPLE 4 n-Octanol was used as an extracting solvent and the extraction was carried out at 50° C., and otherwise in the same manner as in the Example 1, the reaction and consequent purification were carried out. The extraction rates of N-methyl-m-aminophenol, resorcinol and N,N'-dimethyl-m-phenylenediamine into n-octanol were 92.0%, 15.8% and 100, respectively. The removal of the isopropyl ether from the extract by distillation provided N-methyl-m-aminophenol having a purity of 81.3%.

EXAMPLE 5

The amination reaction was carried out in the same manner as in the Example 1. After the reaction, 84.9 g of a 30% aqueous solution of sodium hydroxide was added to the reaction mixture, and extraction was effected using ethyl acetate as an extracting solvent at 50° C. The extraction rates of N-methyl-m-aminophenol, resorcinol and N,N'-dimethyl-m-phenylenediamine into ethyl acetate were 82.7%, 2.3% and 100%, respectively. The removal of the ethyl acetate from the extract by distillation provided N-methyl-m-aminophenol having a purity of 94.8%.

EXAMPLE 6

The extraction was carried out at 70° C., and otherwise in the same manner as in the Example 2, the reaction and consequent purification was carried out. The extraction rates of N-methyl-m-aminophenol, resorcinol and N,N'-dimethyl-m-phenylenediamine into methyl isobutyl ketone were 79.7%, 0% and 100%, respectively. The removal of the methyl isobutyl ketone from the extract by distillation provided N-methyl-m-aminophenol having a purity of 97.5%.

Meanwhile, a 50% aqueous solution of sulfuric acid was added to the aqueous layer separated from the ketone layer and the resultant aqueous mixture was extracted twice with methyl isobutyl ketone, to recover resorcinol having a purity of 99%.

What is claimed is:

1. In the production of an N-alkylaminophenol by the reaction of a divalent phenol with an alkylamine to provide a reaction mixture and recovering the N-alkylaminophenol from the reaction mixture, the improvement comprising:
   (a) adding an aqueous solution of an acid to the reaction mixture in a molar ratio of the acid to the N-alkylaminophenol of 0.5 to 2 to provide a two-phase mixture composed of an aqueous phase which contains a water soluble acid salt of the resultant N-alkylaminophenol and an organic phase which contains an unreacted divalent phenol;
   (b) separating the unreacted divalent phenol as an organic solution by extraction of the two-phase mixture with an organic solvent, to leave an aqueous solution;
   (c) neutralizing the water soluble acid salt of N-alkylaminophenol in the aqueous solution with an aqueous solution of an alkali to provide an oily phase of N-alkylaminophenol; and
   (d) separating the oily phase and distilling it to recover the N-alkylaminophenol.

2. The improvement as claimed in claim 1 wherein the amination reaction is carried out at a temperature of 120°-210° C. in a molar ratio of the alkylamine to the divalent phenol of 0.4-1.2.

3. The improvement as claimed in claim 1 wherein the separated unreacted divalent phenol is reused in the amination reaction.

4. The improvement as claimed in claim 1 wherein the divalent phenol is resorcinol or hydroquinone.

5. The improvement as claimed in claim 1 wherein the alkylamine has the general formula:

wherein $R^1$ and $R^2$ represent independently a hydrogen or an alkyl of 1-6 carbons with both $R^1$ and $R^2$ being not hydrogens.

6. The improvement as claimed in claim 5 wherein the alkylamine is methylamine or ethylamine.

7. In the production of an N-alkylaminophenol by the reaction of a divalent phenol with an alkylamine to provide a reaction mixture and recovering the N-alkylaminophenol from the reaction mixture, the improvement comprising:
   (a) adding an aqueous solution of an alkali to the reaction mixture in an amount of 1 to 3 equivalents per mole of the unreacted divalent phenol to provide a two-phase mixture composed of an aqueous phase which contains a water soluble alkali salt of the resultant unreacted divalent phenol and an organic phase which contains the resultant N-alkylaminophenol;

(b) separating the N-alkylaminophenol from the two-phase mixture by extraction with an organic solvent as an organic solution; and (c) distilling the organic solution to recover the N-alkylaminophenol.

8. The improvement as claimed in claim 7 wherein the amination reaction is carried out at a temperature of 120°–210° C. in a molar ratio of the alkylamine to the divalent phenol of 0.4–1.2.

9. The improvement as claimed in claim 7 wherein the aqueous phase which contains a water soluble alkali salt of the unreacted divalent phenol is neutralized with an aqueous solution of an acid to provide a two-phase mixture composed of an aqueous phase and an oily phase which contains the unreacted divalent phenol, and then the unreacted divalent phenol is recovered for reuse in the amination reaction.

10. The improvement as claimed in claim 7 wherein the divalent phenol is resorcinol or hydroquinone.

11. The improvement as claimed in claim 7 wherein the alkylamine has the general formula:

wherein $R^1$ and $R^2$ represent independently a hydrogen or an alkyl of 1–6 carbons with both $R^1$ and $R^2$ being not hydrogens.

12. The improvement as claimed in claim 11 wherein the alkylamine is methylamine or ethylamine.

13. The improvement as claimed in claim 1 wherein the reaction of the divalent phenol with the alkylamine is carried out in the absence of a solvent at a temperature of 120° to 210° C. under an elevated pressure and under an inert gas atmosphere in the absence of a catalyst to provide the reaction mixture.

14. The improvement as claimed in claim 7 wherein the reaction of the divalent phenol with the alkylamine is carried out in the absence of a solvent at a temperature of 120° to 210° C. under an elevated pressure and under an inert gas atmosphere in the absence of a catalyst to provide the reaction mixture.

* * * * *